(12) United States Patent
Barth et al.

(10) Patent No.: US 6,664,390 B2
(45) Date of Patent: Dec. 16, 2003

(54) METHOD FOR THE SIMPLIFIED PRODUCTION OF (3-CHLORO-4-FLUOROPHENYL)-[7-(3-MORPHOLIN-4-YL-PROPOXY)-6-NITRO-QUINAZOLINE-4-YL]-AMINE OR (3-CHLORO-4-FLUOROPHENYL)-[7-(3-MORPHOLIN-4-YL-PROPOXY)-6-AMINO-QUINAZOLINE-4-YL]-AMINE

(75) Inventors: Hubert Barth, Emmendingen (DE); Klaus Steiner, Emmendingen (DE); Simon Schneider, Emmendingen (DE)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 10/357,814

(22) Filed: Feb. 4, 2003

(65) Prior Publication Data

US 2003/0158408 A1 Aug. 21, 2003

Related U.S. Application Data

(63) Continuation-in-part of application No. 10/204,911, filed as application No. PCT/EP01/00695 on Jan. 23, 2001.

(30) Foreign Application Priority Data

Feb. 2, 2000 (DE) .......................... 100 09 267

(51) Int. Cl.[7] .............................. C07D 413/12
(52) U.S. Cl. ...................................... 544/119
(58) Field of Search ......................... 544/119

(56) References Cited

FOREIGN PATENT DOCUMENTS

WO    WO 97/38983 A1    10/1997

*Primary Examiner*—Robert W. Ramsuer
(74) *Attorney, Agent, or Firm*—Charles W. Ashbrook; Rosanne Goodman

(57) ABSTRACT

The invention concerns a one-pot reaction for the preparation of (3-chloro-4-fluorophenyl)-[7-(3-morpholin-4-yl-propoxy)-6-nitroquinazolin-4-yl]-amine (I)

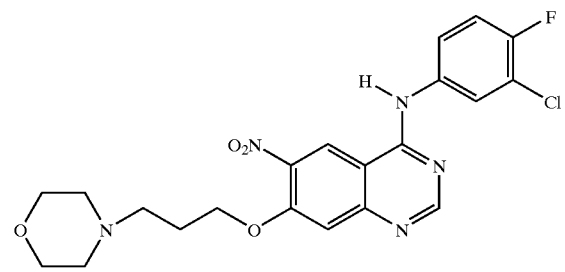

or of (3-chloro-4-fluorophenyl)-[7-(3-morpholino-4-yl-propoxy)-6-aminoquinazolin-4-yl]-amine (VII)

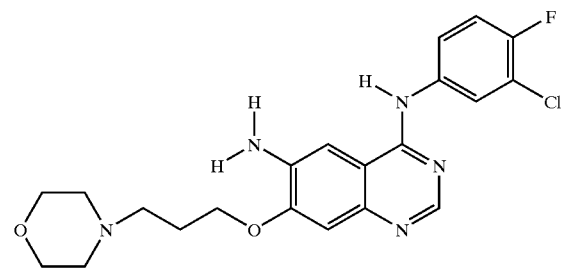

1 Claim, No Drawings

METHOD FOR THE SIMPLIFIED PRODUCTION OF (3-CHLORO-4-FLUOROPHENYL)-[7-(3-MORPHOLIN-4-YL-PROPOXY)-6-NITRO-QUINAZOLINE-4-YL]-AMINE OR (3-CHLORO-4-FLUOROPHENYL)-[7-(3-MORPHOLIN-4-YL-PROPOXY)-6-AMINO-QUINAZOLINE-4-YL]-AMINE

This application is a continuation-in-part of Ser. No. 10/204,911 filed on Aug. 26,2002, now abandoned which is a 371 of PCT /EP01/00695 filed on Jan. 23,2001.

FIELD OF THE INVENTION

The invention concerns a one-pot reaction for the preparation of (3-chloro-4-fluorophenyl)-[7-(3-morpholin-4-yl-propoxy)-6-nitroquinazolin-4-yl]-amine (I) ;

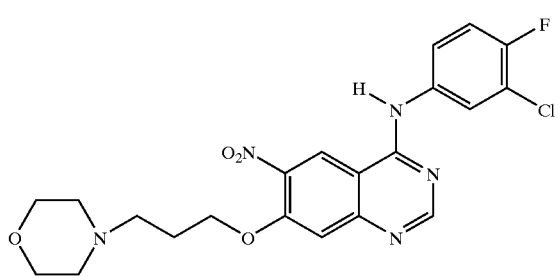

or of (3-chloro-4-fluorophenyl)-[7-( 3-morpholino-4-yl-propoxy)-6-aminoquinazolin-4-yl]-amine (VII)

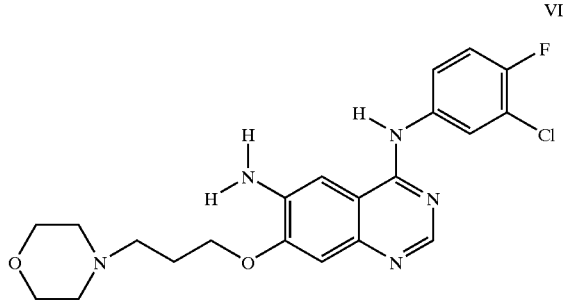

BACKGROUND OF THE INVENTION

The Compound of formula I, (3-chloro-4-fluorophenyl)-[7-(3-morpholin-4-ylpropoxy)-6-nitroquinazolin-4-yl]-amine (I)

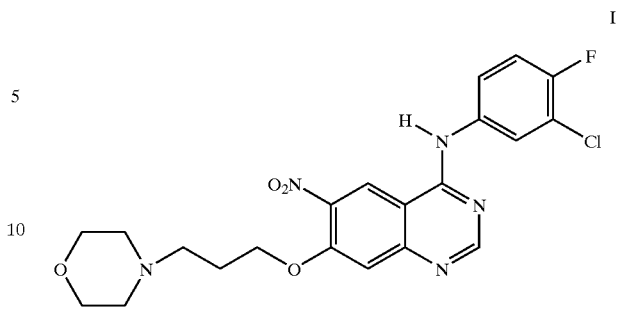

is a key compound for the preparation of N-[4-[(3-chloro-4-fluorophenyl)-amino]-7-[3-( 4-morpholinyl)-propoxy]-quinazolinyl]-propenamide dihydrochloride (II).

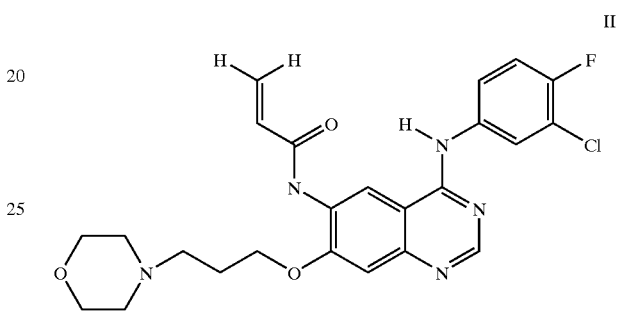

Compound II is representative of a new class of highly effective inhibitors of the EGFR (epidermal growth factor receptor) tyrosine kinase. These inhibitors are useful for the treatment of various tumours, as described, for example, in WO 97/38983.

The original synthesis of compound II is described in J. Med. Chem. 1996, 39, 918–928 and WO 97/38983. The synthesis required 12 steps and was unsuitable for commercial development.

The starting material for the previous synthesis was isomerically pure 7-fluoro-6-nitroquinazolin-4(3H)-one (III)

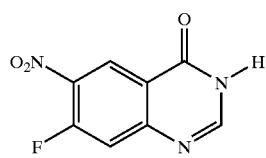

which was reacted with a 55 molar excess of thionyl chloride and catalytic amounts of DMF in the absence of solvent to give 4-chloro-7-fluoro-6-nitroquinazoline (IV)

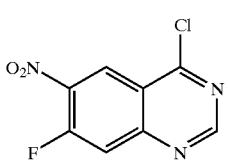

After distilling off of the excess thionyl chloride, the 4-chloro-7-fluoro-6-nitroquinazoline obtained as crude product was reacted portionwise with a solution of 1 equivalent of 3-chloro-4-fluoroaniline and 2 equivalents of the highly toxic N,N-dimethylaniline in 2-propanol. After stirring for 6 hours at 25° C., the solution was subjected to an aqueous work-up comprising washing by mixing from 1–10 times with one or more aqueous solutions, each time removing the aqueous layer and finally obtaining 4-(3-chloro-5-fluoroanilino )-7-fluoro-6-nitroquinazoline (V)

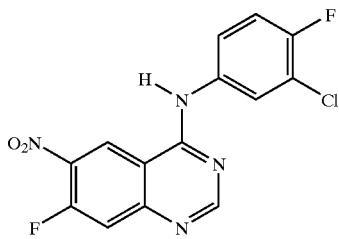

V in about 90% yield as crude product.

To a suspension of 1 equivalent of 4-(3-chloro-4-fluoroanilino)-7-fluoro-6-nitroquinazoline (V) and 1.5 equivalents of 3-(4-morpholino)-propan-1-ol (VI)

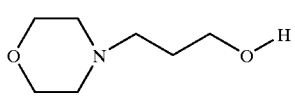

VI in dimethyl sulphoxide (DMSO) was added dropwise a solution of 3 equivalents potassium trimethyl silanoate in DMSO and the reaction mixture was stirred for about 6 hours. After an aqueous working up, (3-chloro-4-fluorophenyl)-[7-(3-morpholin-4-yl-propoxy)-6-nitroquinazolin-4yl]-amine (I) was obtained in about 89% yield.

This synthesis step proved to be especially problematic since, in the case of batch enlargement, variable yields were obtained. Reactions of 4-(3-chloro-4-fluoroanilino)-7-fluoro-6-nitroquinazoline (V), 3-(4-morpholino)-propan-1-ol (VI) and solid sodium hydride in THF, analogously to the process described in WO 97/38983, also lead only to unsatisfactory results.

The (3-chloro-4-fluorophenyl)-[7-(3-morpholin-4-yl-propoxy)-6-nitroquinazolin-4-yl]-amine (I) obtained was subsequently hydrogenated inter alia over Raney nickel in THF as solvent to give (3-chloro-4-fluorophenyl)-[7-(3-morpholin-4-yl-propoxy)-6-aminoquinazolin-4-yl]-amine (VII)

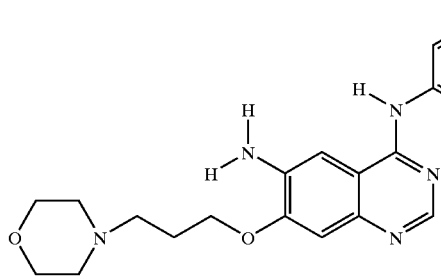

VII and then further reacted to give (II) or its dihydrochloride trihydrate.

SUMMARY OF THE INVENTION

Process for the preparation of (3-chloro-4-fluorophenyl)-[7-(3-morpholin-4-yl-propoxy)-6-nitroquinazolin-4-yl]-amine (I)

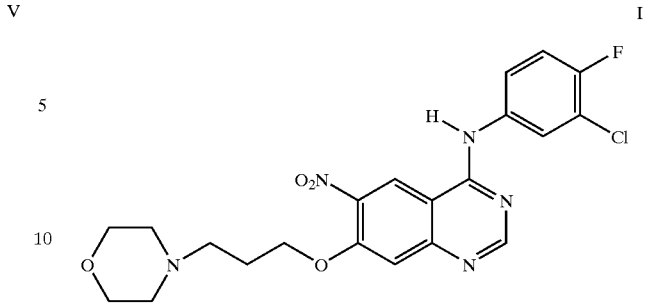

I or of (3-chloro-4-fluorophenyl)-[7-(3-morpholin-4-yl-propoxy)-6-aminoquinazolin-4-yl]-amine (VII)

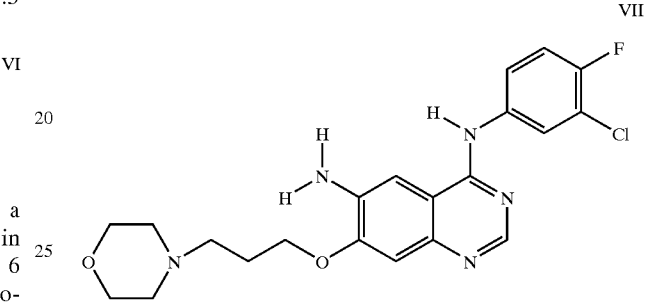

VII characterised in that, in a one-pot reaction, in 3 or 4 reaction steps, one first reacts 7-fluoro-6-nitroquinazolin-4(3H)-one (III)

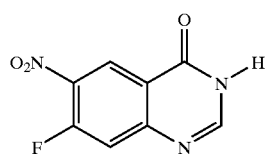

III with thionyl chloride to give 4-chloro-7-fluoro-6-nitroquinazoline (IV)

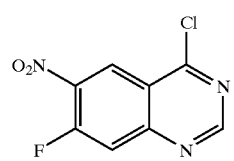

IV then reacts this with 3-chloro-4-fluoroaniline to give 4-(3-chloro-4-fluoroanilino)-7-fluoro-6-nitroquinazoline (V)

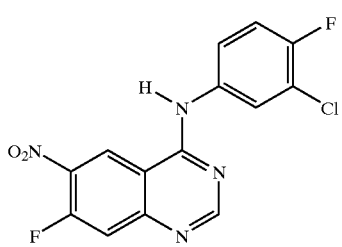

V and subsequently with 3-morpholin-4-yl-propan-1-ol (VI)

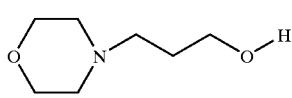

VI to give (I) and possibly hydrogenates (I) directly in the reaction solution to give (VII).

DETAILED DESCRIPTION OF THE INVENTION

This invention provides an economic and technically practical process for the preparation of the above-mentioned key compounds (I) and (VI).

The following issues and difficulties of the prior preparation process that were solved by this invention include the following:

1.) the amount of the thionyl chloride used was be reduced,
2.) the use of the highly toxic N,N-dimethylaniline was avoided,
3.) DMSO was replaced by a cheaper solvent,
4.) potassium trimethylsilanoate or sodium hydride was replaced,
5.) the yields of the reaction of (I) and (VI) must be constantly good,
6.) As far as possible, the isolation of intermediates should be avoided. Therefore, the subject of the invention is the combination of the individual reaction steps to give a one-pot reaction.

Surprisingly, it was found that the chlorination reaction of (III) with thionyl chloride to give (IV), the reaction of the chloride (IV) with 3-chloro-4-fluoroaniline to give (V), and the subsequent reaction of (V) with 3-morpholin-4-yl-propan-1-ol (VI) to give the key compound (I) in outstanding yield can be combined, without isolation of the intermediate compounds, into a one-pot reaction with 3 reaction steps, as illustrated in the reaction scheme (Scheme 1).

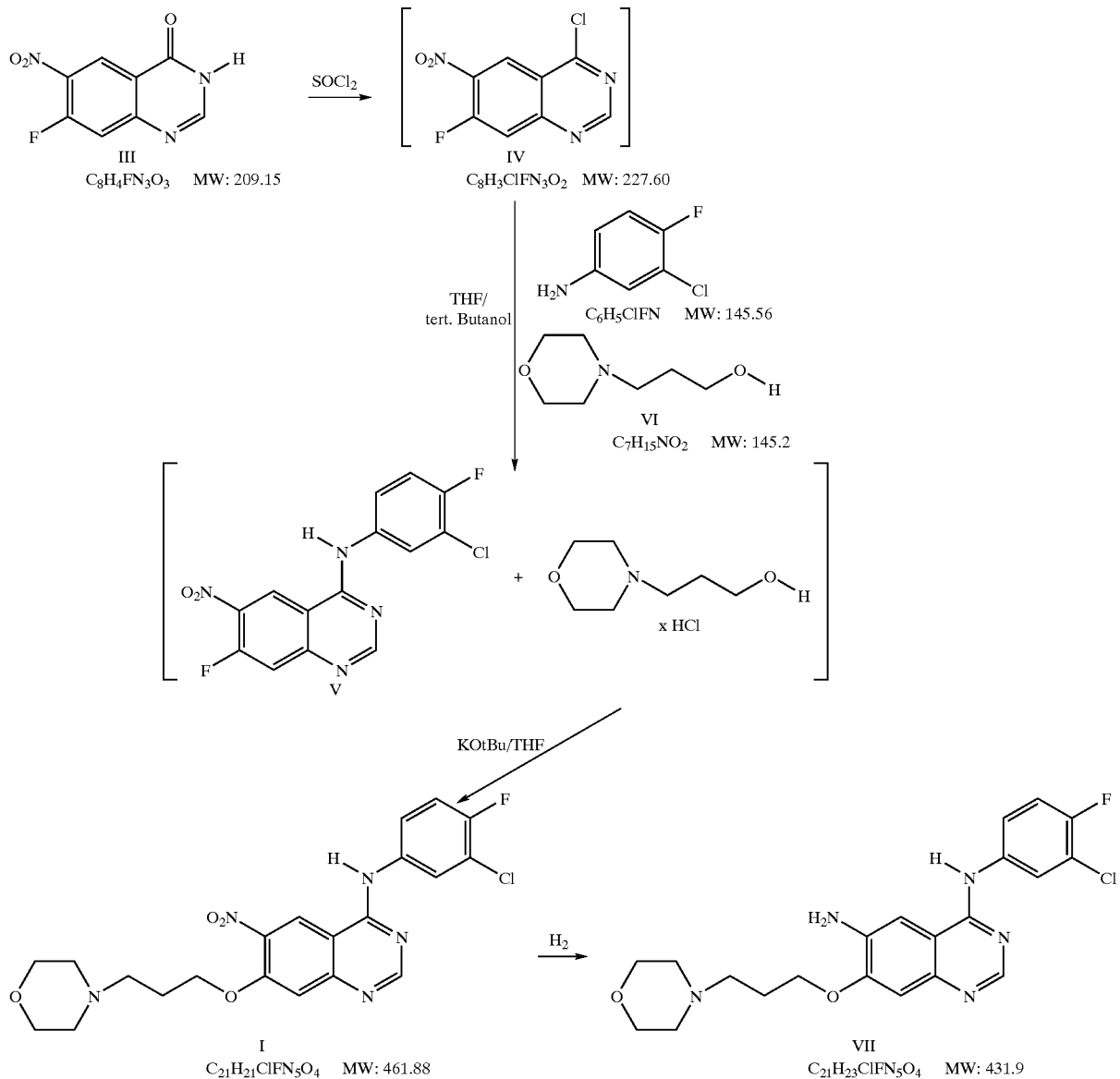

Scheme I

Furthermore, it was, surprisingly, found that it is also not necessary to isolate compound (I) but rather that the reaction mixture obtained in the case of the above-mentioned one-pot reaction can be used directly in the subsequent hydrogenation to give (VII), i.e. to a one-pot reaction with 4 reaction steps.

Furthermore, in the case of the chlorination reaction, the 55 molar excess of thionyl chloride can be reduced to an 11.5 molar excess. After distilling off of the bulk of the thionyl chloride, residual thionyl chloride is distilled off azeotropically several times with toluene. In the case of the last toluene distillation, the toluene must only be distilled off to the extent that a still readily stirrable coarsely crystalline residue remains behind. The so-formed chloride (IV) is very pure and is mixed directly with a tetrahydrofuran/tert.-butanol mixture (7:3). For the further course of the reaction, the use of this tetrahydrofuran/tert.-butanol mixture is of great importance. Surprisingly, it was found that the tert.-butyl alcohol added to the reaction mixture catalyses the desired substitution reaction.

In the following reaction of the chloride (IV) with 3-chloro-4-fluoroaniline, the highly toxic N,N-dimethyl-aniline initially used as acid acceptor could be replaced by the amine necessary in the 3rd reaction step, 3-morpholin-4-yl-propan-1-ol (VI). After about 24 hours stirring at room temperature, the chloride (IV) was completely reacted to give the aniline derivative (V). Surprisingly, the alcohol group of the added base does not react under these conditions. The resulting yellow to orange coloured suspension was mixed directly with a potassium tert.-butylate/THF solution. The 3-morpholin-4-yl-propan-1-ol (VI) used as acid acceptor in the previous step is again converted into the free base which then, in the presence of potassium tert.-butylate, further reacts immediately in the desired way with the aniline derivative (VI) already present in the reaction mixture to give the desired compound (I) which, after quenching with an ice/ethanol/hydrochloric acid mixture, was obtained in a surprisingly good total yield of about 95% with an also surprisingly good purity of about >98%.

This reaction was all the more surprising since the tert.-butyl alcohol present in the reaction mixture does not react with (V) in an analogous manner to the 3-morpholin-4-yl-propan-1-ol (VI) to give the corresponding tert.-butyl ether.

Furthermore, it was surprising that the bases typically used for such substitution reactions (e.g. NaH; WO 97/38983; J. Med. Chem. 35,14, 1992, 2617–2626; J. Am. Chem. Soc. 76,1954, 3032; Heterocycles 22,1, 1984, 73–78. sodium amide (J. Org. Chem. 59, 21,1994, 6194–6199. or potassium trimethylsilonate) could be replaced by potassium tert.-butylate which is much easier to handle on a large scale.

The product (I) was obtained in such high purity that the reaction solution could be used directly for the subsequent hydrogenation without isolation of (I).

The examples presented below are intended to illustrate particular embodiments of the invention, and are not intended to limit the scope of the specification or the claims in any way.

Those having skill in the art will recognize that the starting materials may be varied and additional steps employed to produce compounds encompassed by the present invention, as demonstrated by the following examples. The following examples are for illustrative purposes only and are not intended, nor should they be construed as limiting the invention in any manner. Those skilled in the art will appreciate that variations and modifications can be made without violating the spirit or scope of the invention.

Example 1

One-pot Reaction for the Preparation of (3-chloro-4-fluorophenyl)-[7-( 3-morpholin-4-yl-propoxy)-6-nitroquinazolin-4-yl]-amine (1).

150 g 7-fluoro-6-nitroquinazolin-4(3H)-one (III) are suspended in 600 ml thionyl chloride and, after addition of 6 ml DMF, boiled under reflux for 24 hrs. A clear solution hereby results. About 350 ml thionyl chloride are distilled off in a vacuum. The resulting coarsely crystalline suspension is mixed with about 600 ml toluene. About 800 ml are distilled off in a vacuum. This distillation was further repeated 3 times with, in each case, 600 ml fresh toluene. In the case of the last distillation, the toluene is distilled off as far as possible. There results a coarsely crystalline suspension which, at all times, remains well stirrable.

The almost dry residue is mixed with 1.2 l of a tetrahydrofuran/tert.-butanol mixture (7:3). The resulting suspension is cooled to about 10° C. With good stirring and cooling, a solution of 114 g 3-chloro-4-fluoroaniline and 258 g 3-morpholin-4-yl-propan-1-ol (VI) in 300 ml THF/tert.-butanol (7:3) is added dropwise over the course of about 20 min. so that the temperature in the reactor remains between 10° C. and 15° C. The initially yellowish suspension becomes thinner and colours orange in the course of the addition.

One allows the reaction mixture slowly to come to room temperature and subsequently stirs it at room temperature for at least 24 hrs.

To the yellow-orange suspension is added dropwise, with good stirring and gentle cooling during the course of about 20 min., a solution of 324 g potassium tert.-butylate in 1.86 l tetrahydrofuran so that the temperature in the reactor remains between 15° C. and 20° C. After addition of about ⅓ of the potassium tert.-butylate/THF solution, the whole reaction mixture becomes dark red coloured.

After about 30 minutes of further stirring, the mixture is immediately stirred into a mixture of 5.4 kg ice, 6.0 l ethanol and 1.8 l hydrochloric acid (pH of the solution about 8). There hereby first results a yellow-orange solution. After brief stirring, a yellow product crystallizes out. The resulting suspension is further stirred for about 5 hrs at about 0° C. and subsequently filtered with suction. The filter cake is washed twice with, in each case, 500 ml ice-cold ethanol.

The product is pre-dried in a circulating air cabinet first at 40° C. and subsequently at 60° C. to constant weight (yield: 316.5 g =95.5%; HPLC purity: 98.48 rel. % ; $H_2O$ (K.F.) 3.69% m.p. 257° C.

Example 2

One-pot Reaction for the Preparation of (3-chloro-4-fluorophenyl)-r7-( 3-morpholin-4-yl-propoxy)-6-aminoquinazolin-4-yl1-amine (VII).

20 g 7-fluoro-6-nitroquinazolin-4-(3H)-one (III) are suspended in 80 ml thionyl chloride and, after addition of 20 drops of DMF, boiled under reflux for 24 hrs. A clear solution hereby results. About 60 ml thionyl chloride are distilled off in a vacuum. The resulting coarsely crystalline suspension is mixed with about 60 ml toluene. About 60 ml are distilled off in a vacuum. This distillation is repeated 3 times with, in each case, 60 ml fresh toluene. In the last distillation, the toluene is distilled off as far as possible. There results a coarsely crystalline suspension which at all times remains well stirrable.

The almost dry residue is mixed with 160 ml of a tetrahydrofuran/tert.-butanol mixture. The resulting suspension is cooled to about 10C. With good stirring and cooling, a solution of 15.2 g 3-chloro-4-fluoroaniline and 34.4 g 3-morpholin-4-yl-propan-1-ol (VI) in 40 ml THF/tert.-butanol (7:3) is added dropwise over the course of about 20 min. so that the temperature in the reactor remains between 10° C. and 15° C. The initially yellow suspension becomes thinner during the addition and turns orange.

One allows the reaction mixture to come slowly to room temperature and subsequently stirs for at least 24 hrs. at room temperature.

To the yellow-orange suspension is added dropwise, with good stirring and gentle cooling over the course of about 20 min., a solution of 43.2 g potassium tert.-butylate in 250 ml tetrahydrofuran so that the temperature in the reactor remains between 15° C. and 20° C. After addition of about ⅓ of the potassium tert.-butylate/THF solution, the whole reaction mixture becomes dark red coloured.

After stirring for about 30 minutes further, the reaction mixture is mixed at 0° C.–5° C. with a mixture of 20 ml hydrochloric acid and 30 ml water and diluted with a further 200 ml THF. After stirring for 20 minutes in an ice bath, the reaction mixture is filtered clear over 50 g Celite. The filter cake is rinsed with 100 ml THF. The filtrate is mixed with 31 g Raney nickel and hydrogenated at room temperature for 3 hrs. at 3.5 bar with hydrogen. After filtering off the catalyst with suction, the filtrate is evaporated to dryness and the residue stirred with 80 ml ethanol at about 2° C. The precipitated product is filtered off with suction and washed with a little cold ethanol. After drying in a circulating air drying cabinet at 60° C., there are obtained 32.1 g (77.7%) of product.

What is claimed is:
1. Process for the preparation of (3-chloro-4-fluorophenyl)-[7-(3-morpholin-4-yl-propoxy)-6-nitroquinazolin-4-yl]-amine (1)

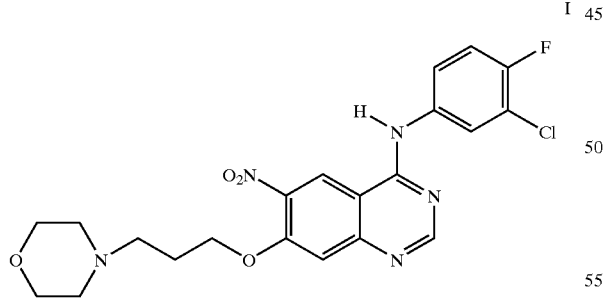

I or of 3-chloro-4-fluorophenyl)-[7-(3-morpholin-4-yl-propoxy)-6-aminoquinazolin-4-yl]-amine (VII)

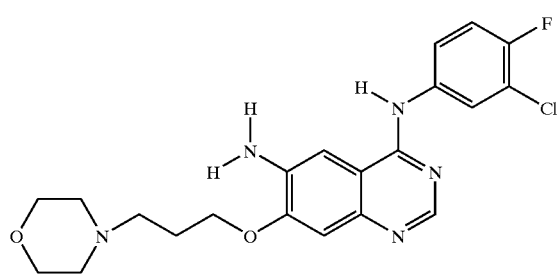

VII characterised in that, in a one-pot reaction, in 3 or 4 reaction steps, one first reacts 7-fluoro-6-nitroquinazolin-4(3H)-one (III)

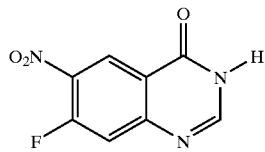

III with thionyl chloride to give 4-chloro-7-fluoro-6-nitroquinazoline (IV)

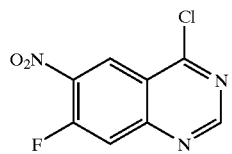

IV then reacts this with 3-chloro-4-fluoroaniline to give 4-(3-chloro-4-fluoroanilino)-7-fluoro-6-nitroquinazoline (V)

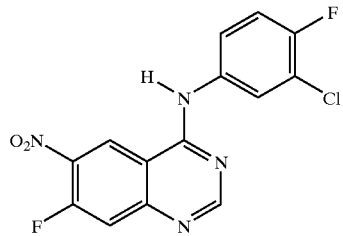

V and subsequently with 3-morpholin-4-yl-propan-1-ol (VI)

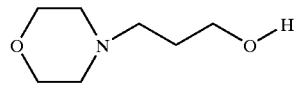

VI to give (I) and optionally hydrogenates (I) directly in the reaction solution to give (III).

* * * * *